United States Patent [19]

Waltke

[11] 4,240,605
[45] Dec. 23, 1980

[54] JIG ASSEMBLY FOR PREPARING DENTAL IMPRESSIONS FOR CASTING

[75] Inventor: Robert W. Waltke, Bayside, N.Y.

[73] Assignee: Pennwalt Corporation, Philadelphia, Pa.

[21] Appl. No.: 75,931

[22] Filed: Sep. 17, 1979

[51] Int. Cl.³ .................. A61C 5/10; A61C 13/08
[52] U.S. Cl. ...................... 249/54; 249/48; 249/51; 249/139; 433/74
[58] Field of Search ............ 249/54, 48, 51, 165; 433/74

[56] References Cited

U.S. PATENT DOCUMENTS

| 783,901 | 2/1905 | Sheldon | 249/51 |
|---|---|---|---|
| 1,119,711 | 12/1914 | McGee | 249/51 |
| 1,204,166 | 11/1916 | Levin | 249/54 |
| 3,469,316 | 9/1969 | Stern et al. | 249/54 |
| 3,553,839 | 9/1969 | Gores | 433/74 |
| 3,798,772 | 3/1974 | Eberhard | 433/74 |
| 4,056,585 | 11/1977 | Waltke | 249/54 |

Primary Examiner—Murray Tillman
Assistant Examiner—A. H. Koeckert

[57] ABSTRACT

Improved apparatus for positioning and suspending paraphernalia in a dental negative mould comprising a pair of pins insertable into the mould along the bucco-lingual midline of the tooth to be made detachable from the remainder of the dental cast or model. The paraphernalia articulates with the pins and is precisely positionable in the mould due to unique structure of the jig assembly and paraphernalia, or tooth die forming member, which permits movement of the latter along or rotation about three different axes.

18 Claims, 14 Drawing Figures

U.S. Patent   Dec. 23, 1980   Sheet 1 of 3   4,240,605
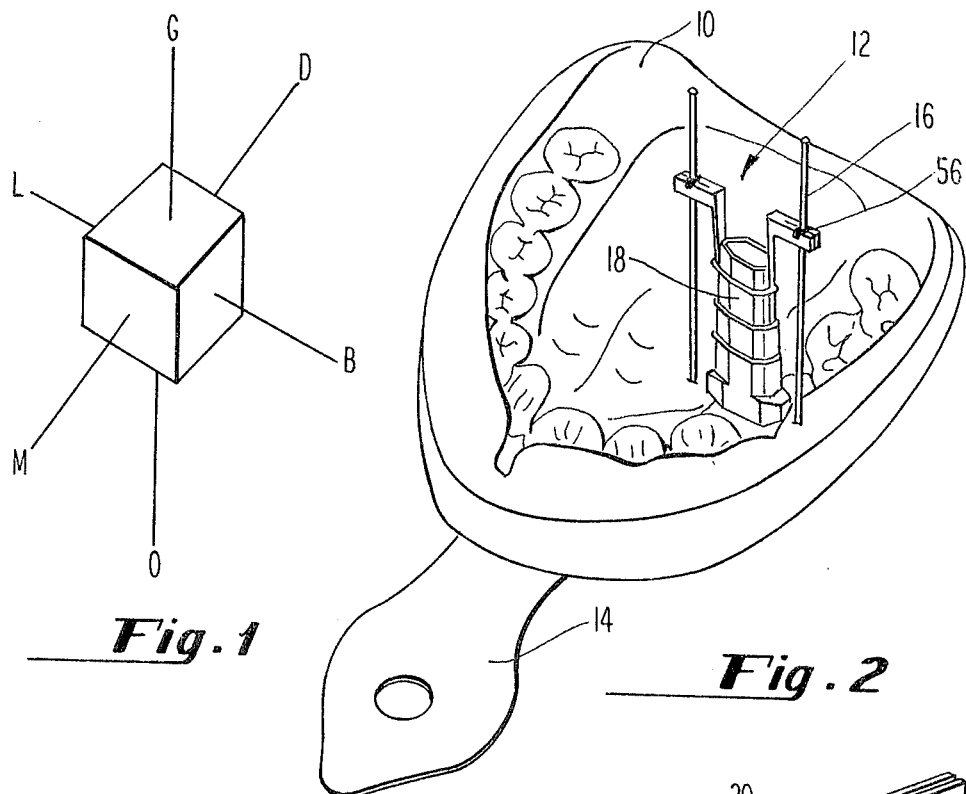
Fig. 1
Fig. 2
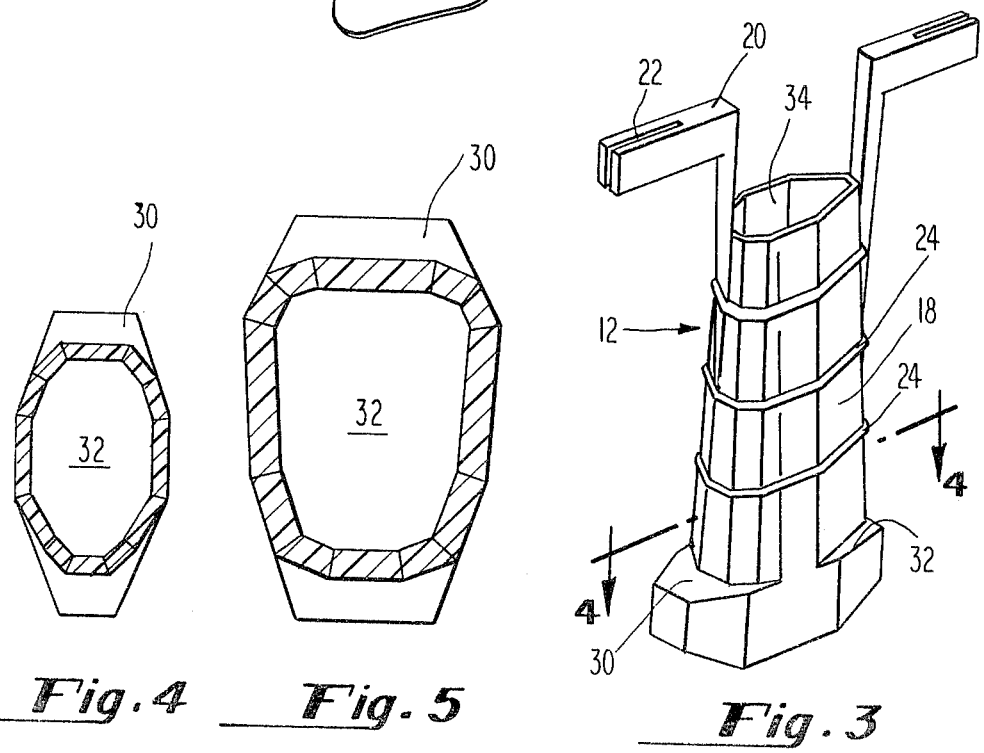
Fig. 4   Fig. 5   Fig. 3

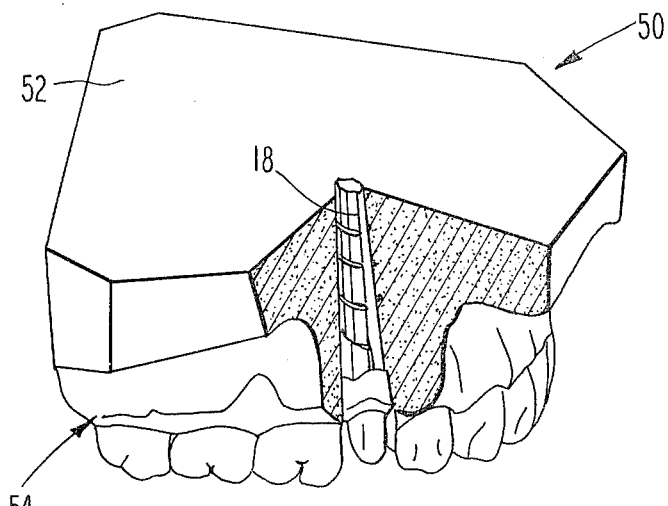
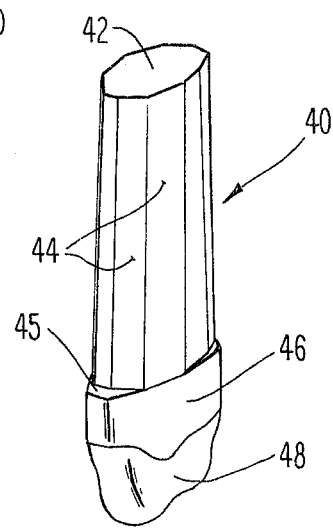
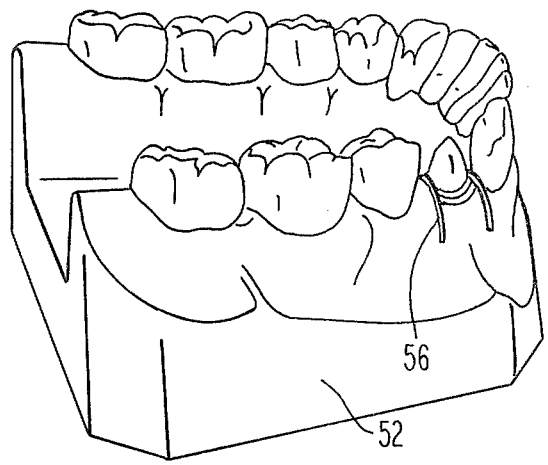
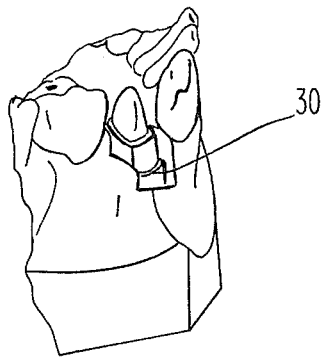
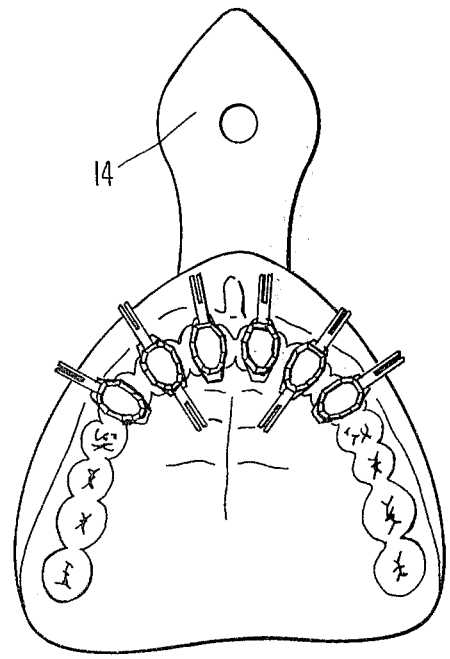

JIG ASSEMBLY FOR PREPARING DENTAL IMPRESSIONS FOR CASTING

STATEMENT OF THE INVENTION

This invention relates to making models of teeth and more particularly to prosthetic dentistry whereby one section of a dental casting is separable from the remainder thereof.

BACKGROUND AND SUMMARY OF THE INVENTION

In that aspect of dentistry which relates to tooth restoration, it is often required that an accurate dental model be made in a dental stone material of the affected tooth or teeth and the surrounding tissue areas. Many and various methods are known in the industry for providing such a model. In most such methods, paraphernalia including dowels, parting plates, sleeves, and the like, are positioned in the dental negative mould prior to the casting of any dental stone thereinto. The selected paraphernalia is traditionally fixed in the impression by one of several methods, as by luting the paraphernalia onto the inner wall of the impression with wax; or, a cross-member, suitably a paper clip, bobby pin, or match stick, is luted transversely across inner walls of the impression, i.e., from the buccal or labial wall to the palatal area, and then luting the dowel, sleeve, or dowel and parting plate assembly perpendicularly to the cross-member; or, the impression may be attached to a flask member of a complicated flask and superstructure arrangement wherein lugs provided on the flask member engage mating counterparts on the superstructure.

Regardless of the method used, a slurry of dental stone is then poured into the impression. If the flask/superstructure device is employed, the superstructure will be lowered into the slurry while the slurry is still soft.

The prior art methods and/or apparatus above-described, while generally satisfactory, suffer deficiencies and weaknesses substantially overcome by the present invention. For example, after carefully removing the separable or removable section or portion, i.e., the tooth die or dies, from the model, it was difficult to keep the dies in their original alignment. Repeated removals and insertions of the dies from and into the model further contributed to the poor alignment.

Also, if a dowel or mounting pin is employed in order to facilitate handling the tooth die as well as its repositioning back into the model or base stone, it was oftentimes difficult to accurately position a dowel relative to the negative impression of the tooth to be worked on. It is essential that a dowel be maintained in a substantially vertical position in the center of the impression of the tooth for proper removal of the tooth die. If a jig is used to hold the dowel, the vertical and lateral adjustment of the jig was difficult to manage.

Even where dowels are not required, as taught, for example, in U.S. Pat. No. 4,056,585, issued to the present applicant, protrusions or extensions on the outer surfaces of the die former are needed to assure the non-removability of the die former from the mould. Eye extensions, for passage therethrough of supporting pins which are pressed into the soft impression material for positioning the die former, are also required.

The present invention provides a jig which permits paraphernalia to be simply and precisely positioned within a negative dental mould or impression and requiring no dowels, parting plates, protrusions or extensions.

More specifically, the present invention comprises a pair of straight pins which are inserted into the negative impression substantially parallel to the root and crown axis of the affected tooth. A die forming member is provided with a pair of opposed laterally extending slotted tabs which engage the pins to thus permit versatile movement and precise positioning of the die forming member.

BRIEF DESCRIPTION OF THE DRAWINGS

FIG. 1 illustrates a cube which represents the six sides of a typical tooth.

FIG. 2 is a perspective view of a dental negative impression and tray with which the mounting jig of the present invention may be beneficially used.

FIG. 3 is a perspective view of the tooth die former which forms a part of the mounting jig shown in FIG. 2.

FIG. 4 is a sectional view of the die former of FIG. 3 taken along line 4—4 thereof illustrating an ovoid configuration for use with anterior and bicuspid dies.

FIG. 5 is a view similar to FIG. 4 illustrating a die former having a modified keystone configuration for use with molar dies.

FIG. 6 is a perspective view of a finished unitary tooth die.

FIG. 7 is a perspective view, partially cutaway, of a dental model illustrating retention of the die former therewithin.

FIG. 8 is a perspective view of the model of FIG. 7 illustrating the approximate locations of proximal saw cuts to be made in removing or separating the tooth die.

FIG. 9 is a perspective view of the tooth die of FIG. 8 which illustrates a further step in the removal of the tooth die from the model.

FIG. 10 is a plan view of the dental negative mould of FIG. 2 illustrating placement of die formers when making multiple anterior dies and showing removal of appropriate mounting tabs therefrom.

DETAILED DESCRIPTION OF THE INVENTION

Figure 11:
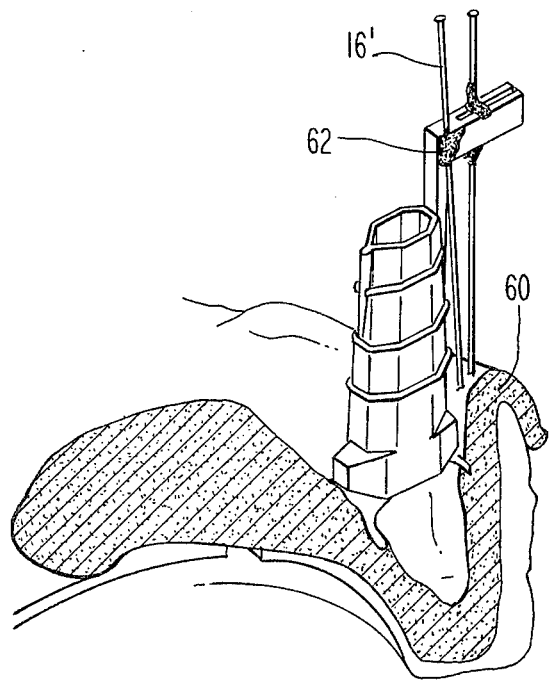
FIG. 11 is a perspective view illustrating position of a die former when used with a small anterior arch.

If an artificial tooth such as a denture tooth or a pontic tooth, for example, is considered to be a six-sided solid, such as a cube, for example, then three intersecting axes, each perpendicular to each other, will be formed if lines are drawn through the centers of opposing sides of the cube. In FIG. 1, the three axes are designated by letters MD, BL, and GO, where M represents one side of a tooth, the mesial side, or that side of the tooth which faces the median line of the dental arch; and D represents the distal side, or that side of the tooth which faces away from the median line. Side B is the buccal side of the tooth, or that side which faces the cheek whereas the tongue or lingual side of the tooth is designated L. That portion of the tooth which is bordered by the gingival or gum tissue is designated G, and O represents the occlusal or biting side of the tooth. Thus, line MD may be referred to as the mesiodistal axis and lines BL and GO as the buccolingual axis and gingivo-occlusal axis respectively.

The jig assembly of the present invention is utilized for precisely positioning or suspending the paraphernalia or tooth die forming member in a fixed position in the negative dental mould, which position is determined by fixing the paraphernalia, or tooth die forming member, with respect to 3 axes, i.e., mesiodistal axis MD, buccolingual axis BL, and gingivo-occlusal axis GO.

Since the tooth die forming member, or sleeve, forms the stem of the tooth die and not the crown of the tooth die, the sleeve will be positioned several millimeters above the intersection of the 3 axes, which axes are located at the cener of the crown of a tooth. The long axis of the die forming sleeve is coincident with the gingivo-occlusal axis GO (FIG. 1).

In FIG. 2, a wax or rubber negative or elastic mould or impression of the patient's teeth and gums supports the mounting jig 12 of the present invention, each being supported on a dental tray 14.

It is common practice, when making a model of a patient's teeth, to first form a negative impression thereof. The negative impression is filled with a die material to form a positive replica of the teeth. After the die material has cured or set, the model is completed by casting a base stone formed integrally with the die material to form a foundation for the replica of the teeth. A tooth die which is to be worked on is made removable from the model by cutting the die material by suitable means and separating the tooth die therefrom.

In preparing impression 10 for casting a removable tooth die, a pair of straight pins 16 is inserted substantially vertically in the impression on the buccolingual midline of the tooth that is to be removed or separated from the model. A hollow die forming member 18, or sleeve, or casting member, articulates with pins 16 in order that the die forming member may be precisely positioned. Die former 18, clearly illustrated in FIG. 3, is suitably injection moulded from a tough abrasion resistant plastic which is solvent-proof and capable of withstanding boiling water. The die former includes a pair of opposed laterally extending mounting tabs 20, each having a slot 22 disposed therein along a substantial portion of its length for engaging mounting pins 16. Mounting tabs 20, in effect, is an interrupted bar member. Such a bar member may readily be employed, which bar member may be provided with a central hole which would not only permit viewing into the sleeve, but also for receiving a dowel member, a dowel and parting plate assembly, and the like. Spaced retention rings 24 are moulded about the die former 16 to assist in its permanent retention within the model. Since the die former is permanently retained in the model base, tooth dies and their precision moulded stems may be cast simultaneously. A shoulder 30 is provided on die former 18, its purpose later to be described. The die former, comprising a portion of the jig assembly of the present invention, is available in a plurality of different sizes which includes two basic cross-sectional configurations. The smaller die formers, i.e., the 3,4,5, and 6 mm. sizes, which represent the mesiodistal width, have an ovoid configuration, as illustrated in FIG. 5, and are used for all anterior and bicuspid dies. The molar dies employ the 7 and 8 mm. sizes and have a modified keystone cross-section (FIG. 5). Of course, the invention is not intended to be limited to the sizes and shapes described and illustrated.

The interior of die former 18 is hollow and tapers from the wider end opening 32 adjacent shoulder 30 toward the narrower end opening 34 adjacent mounting tabs 20. Thus, when a tooth die is formed within the die former and is removed therefrom, such tooth die can be returned to the interior thereof only in the same position that it assumed originally when it was cast. Hence, die former 18 and tooth die formed therein must assume only one predetermined relationship and no other.

In FIG. 6, tooth die 40 comprises die stem 42 which is a replica of the interior of die former 18 and includes flats 44 corresponding to the flats of the die formers illustrated in FIGS. 4 and 5. The tooth die has a shoulder portion 45, apron 46, and prepared tooth 48. It is apparent that the tooth die may be repositioned within the model 50 of FIG. 7 in only one predetermined relationship, as above-mentioned. Model 50 includes the die forming member 18 which is permanently retained therewithin, stone base 52, cast teeth and gum areas 54 including the tooth die 40.

In making the tooth die of FIG. 6, the proper size die former is selected, which die former should have the same mesiodistal diameter as the prepared tooth. The die former may be slightly narrower than the prepared tooth. It should not, however, be wider, or encroachment upon adjacent teeth might result. The buccolingual dimension of the die former may be smaller or larger than, or the same size as, the prepared tooth dimensions.

Insert the two straight pins 16 into the impression 10, one bucally and the other lingually, centered on the buccolingual midline of the tooth that is to be separated from the model. Travel or movement of the die former, or die forming sleeve 18 along an axis, or rotation thereof about an axis, is determined by the placement of pins 16, i.e., the pins may be positioned vertically in the negative dental mould, or angled toward the mesial or distal areas thereof. Die former 18 may now be articulated with pins 16 by means of slots 22 of tabs 20 engaging pins 16. Movement of the tabs along gingivo-occlusal axis GO may be accomplished by moving the die former substantially vertically along pins 16; and along the buccolingual axis BL by sliding the tabs back and forth such that one of the pins 16 is more deeply engaged in its respective slot. Rotation of the die former about the mesiodistal axis MD is effected by tilting the tabs buccally or lingually substantially along the buccolingual plane defined by axis BL, which tilting is considered a limited rotation of the die former about the mesiodistal axis MD.

After the die former has been properly centered with respect to the negative tooth impression over which it is directly suspended, i.e., its position is precisely related to the intersection of, and the necessary degree of rotation about, the 3 axes of the tooth associated therewith, a hard resinous wax is flowed into the slots 22 of tabs 20 around pins 16 for sealing the contact therebetween, as indicated by the numeral 56 of FIG. 2.

The bottom of the shoulder portion 30 of die former 18 should form a gap of about 3 to 4 mm. above the peripheral margin of the tooth preparation. Apron 46 of the tooth die is determined by this gap distance.

The impression is now boxed with boxing wax, or alternatively, wrapped with a suitable masking tape. An aerosol liquid surface tension breaker may be applied at this point, if required. Upon drying of the surface tension breaker, if used, the model may be poured. No attempt should be made to fill the die former as the stone or epoxy will seep thereinto and seek its own level as it proceeds to fill the boxing wax. If epoxy is used however, for purposes of economy, enough material is poured into the impression to fill the prepared teeth. The model may then be centrifuged before additional epoxy is added, up to the second or third retention ring on the die former.

When the model is hard, separate it from the impression and extract pins. The model base may now be trimmed to size and shape and the mounting tabs snipped or ground off. A proximal saw cut 56 (FIG. 8) to a depth of about 4–6 mm. deep is made on each side of the tooth die to be removed. A small fissure bur or tapered stone may now be used to find or expose the buccal and lingual shoulder of the die former shoulder 30 (FIG. 9) by gradually and carefully trimming back the stone or epoxy between the saw cuts. The die former shoulder should not be damaged as its unobliterated presence is required to fully and completely reposition and seat the tooth die in the model by sight and feel.

The tooth die may now be tapped out with any suitable device and the tooth die trimmed, again exercising care to preserve its shoulder 45.

The adaptability of the present invention to accommodate varying dental arch shapes and its versatility in precisely positioning and suspending paraphernalia, even where prepared tooth dies are contiguously disposed, is worthy of note. For example, when multiple anterior dies are made, the lingual mounting tabs of the die formers may interfere with each other and should be clipped off. The impression may then be set up as shown in FIG. 10.

When the patient has a very small anterior arch, removal of all lingual mounting tabs may be required. In such case, an additional pin 16 may be placed in the labial flange 60 of the impression and luted thereto as indicated at 62 (FIG. 11).

Figure 12:
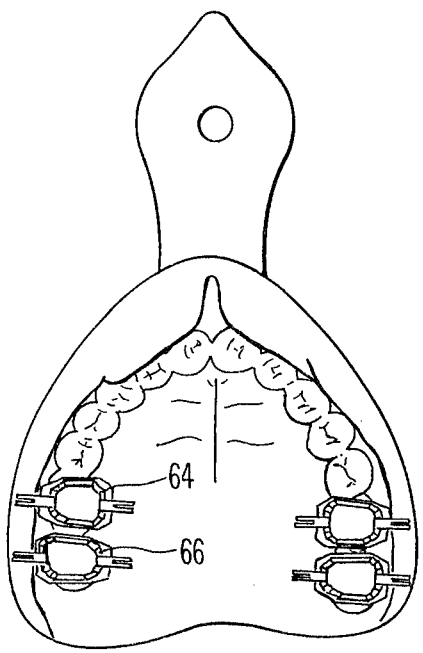
FIG. 12-14 are plan views of a negative dental mould with recommended die former orientation for molars in various type dental arches.

A normal arch is shown in FIG. 12. As aforementioned, the molar dies employ the larger die formers which have a modified keystone cross-section. The wide base 64 of the keystone is employed as the lingual aspect of the die former for the first molars whereas the second molars employ the narrow base 66 thereat.

Figure 13:
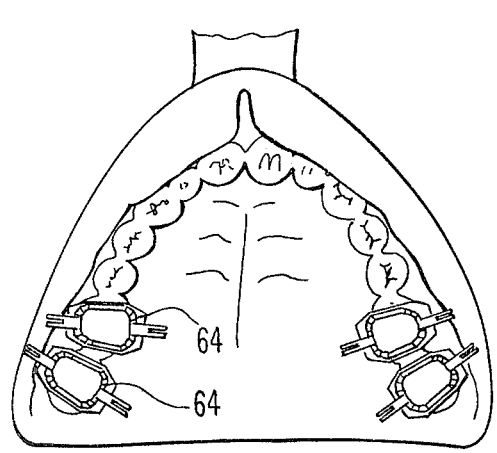

A patient with a tapered arch form may require the wide base 64 of the keystone as the lingual aspect of the die former for both first and second molars (FIG. 13).

Figure 14:
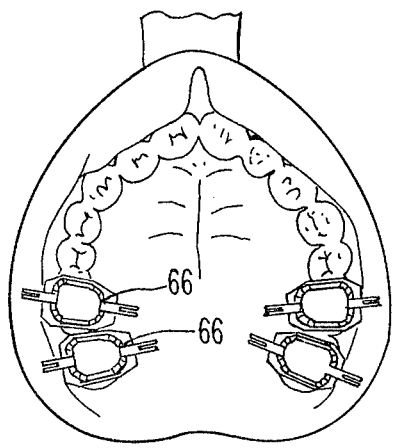

An impression with a rounded arch form could benefit from having the wide base 66 of the keystone as the buccal aspect of the die former for both first and second molars (FIG. 14).

I wish it to be understood that I do not desire to be limited to the details of construction and geometry shown and described herein for obvious modifications will occur to a person skilled in the art without departing from the spirit of the invention.

I claim:

1. A jig assembly for precisely positioning paraphernalia means such as die forming means and the like with respect to a negative tooth impression provided in a negative dental mould for use in casting a dental model having at least one unitary tooth die including a stem and prepared tooth, said prepared tooth replicating said tooth forming said negative tooth impression, said unitary tooth die being removable from said model, said jig assembly comprising pin means insertable in said dental mould adjacent said negative tooth impression and paraphernalia means, said paraphernalia means being open ended and articulating with said pin means and positionable above said negative tooth impression in spaced relationship thereto, said paraphernalia means being continuously movable with respect to said pin means in directions substantially parallel with long axis of said pin means, and continuously movable along a plane defining buccolingual midline of said negative tooth impression normal to said pin means long axis, and continuously tiltable in said plane away from perpendicularity with said pin means long axis, and combinations of said directions; said paraphernalia means having a hollow interior for receiving die material poured into said dental mould to form said stem of said unitary tooth die, said interior of said paraphernalia means replicating configuration of said stem.

2. Jig assembly of claim 1 wherein said paraphernalia means comprises tooth die forming means.

3. Jig assembly of claim 2 wherein said pin means comprises a pair of straight pins.

4. Jig assembly of claim 2 wherein said open ended die forming means includes a tapered sleeve being smaller at one of its ends than at the other of its ends.

5. Jig assembly of claim 4 wherein said spaced relationship between said open ended die forming means and negative tooth impression defines a space about 3 to 4 mm., said space defining an apron on said unitary tooth die formed between said stem and said prepared tooth.

6. Jig assembly of claim 5 wherein said sleeve is provided with a shoulder adjacent larger end thereof and wherein space provided between said shoulder and peripheral margin of said tooth negative impression defines said apron portion of said unitary tooth die.

7. Jig assembly of claim 6 wherein said die forming means includes pin engaging means disposed at smaller end of said sleeve.

8. Jig assembly of claim 7 wherein said die forming means includes a pair of opposed laterally extending mounting tabs at smaller end of said sleeve.

9. Jig assembly of claim 8 wherein each of said mounting tabs is provided with a slot starting at its outer portion and running substantially the length of said tab, said slots being in alignment.

10. Jig assembly of claim 9 wherein said sleeve defines a configuration which prevents insertion of said stem of said removable tooth die thereinto except in one predetermined position.

11. Jig assembly of claim 10 wherein said sleeve has a cross-section of substantially ovoid configuration.

12. Jig assembly of claim 10 wherein said sleeve has a cross-section of substantially modified keystone configuration.

13. Jig assembly of claim 10 wherein said sleeve is provided with a plurality of spaced parallel retention rings therearound to insure retention of said die forming means permanently within said model.

14. Jig assembly of claim 13 wherein a plurality of said mounting jigs precisely superpose said die forming means over said negative tooth impressions of said negative dental mould for making multiple anterior tooth dies, one of said pair of mounting tabs being removed when mounting tabs of adjacent die formers are disposed in interfering relationship.

15. Jig assembly of claim 13 wherein said negative dental mould includes a very small anterior arch and a labial flange, and wherein said pair of straight pins are inserted into said labial flange, both of said pins articulating with and luted to said mounting tab buccally disposed.

16. Jig assembly of claim 13 wherein a plurality of mounting jigs precisely superpose said die forming means over negative molar impressions of said negative dental mould of a normal arch for making multiple molar tooth dies, said sleeves of said die forming means having a modified keystone cross-section with a wide base and a narrow base, said wide base of the sleeve forming lingual aspect thereof for the first molars and said narrow base of the sleeve forming buccal aspect of the sleeve for the second molars.

17. Jig assembly of claim 13 wherein a plurality of mounting jigs precisely superpose said die forming means over negative molar impressions of said negative dental mould of a tapered arch for making multiple molar dies, said sleeves of said die forming means having a modified keystone cross-section with a wide base and a narrow base, said wide bases of the sleeves forming lingual aspects thereof for both first and second molars.

18. Jig assembly of claim 13 wherein a plurality of mounting jigs precisely superpose said die forming means over negative molar impressions of said negative dental mould of a rounded arch for making multiple molar tooth dies, said sleeves of said die forming means having a modified keystone cross-section with a wide base, said wide bases of the sleeves forming buccal aspects thereof for both first and second molars.

* * * * *